United States Patent
Ross et al.

(10) Patent No.: US 10,506,953 B2
(45) Date of Patent: Dec. 17, 2019

(54) OPERATION-VERIFYING WEARABLE VAPOR SENSOR

(71) Applicant: BIOINTELLISENSE, INC., Redwood City, CA (US)

(72) Inventors: Mark Ross, San Carlos, CA (US); David Wang, Palo Alto, CA (US)

(73) Assignee: BIOINTELLISENSE, INC., Redwood City, CA (US)

(*) Notice: Subject to any disclaimer, the term of this patent is extended or adjusted under 35 U.S.C. 154(b) by 81 days.

(21) Appl. No.: 15/639,636

(22) Filed: Jun. 30, 2017

(65) Prior Publication Data

US 2019/0000357 A1    Jan. 3, 2019

(51) Int. Cl.
*A61B 5/145* (2006.01)
*A61B 5/00* (2006.01)
*A61B 5/01* (2006.01)

(52) U.S. Cl.
CPC ............ *A61B 5/14517* (2013.01); *A61B 5/01* (2013.01); *A61B 5/681* (2013.01); *A61B 5/6815* (2013.01); *A61B 5/6843* (2013.01)

(58) Field of Classification Search
CPC ..... A61B 5/14517; A61B 5/6815; A61B 5/01; A61B 5/681; A61B 5/6843
See application file for complete search history.

(56) References Cited

U.S. PATENT DOCUMENTS

| | | | |
|---|---|---|---|
| 4,066,068 A * | 1/1978 | Nilsson | A61B 5/4283 600/307 |
| 4,940,330 A | 7/1990 | Dopheide et al. | |
| 2007/0083095 A1 | 4/2007 | Rippo et al. | |
| 2008/0316037 A1 * | 12/2008 | Shoji | B60K 28/063 340/576 |
| 2014/0206945 A1 * | 7/2014 | Liao | A61N 1/0529 600/301 |

(Continued)

FOREIGN PATENT DOCUMENTS

| | | |
|---|---|---|
| GB | 1532419 A1 | 11/1978 |
| WO | 2015192539 A1 | 12/2015 |
| WO | 2016033496 A1 | 3/2016 |

OTHER PUBLICATIONS

Nobutomo Morita et al., "Development of a Built-In Micro-Laser Doppler Velocimeter", Apr. 2016, https://ieeexplore.ieee.org/document/7397850, Nov. 9, 2018.*

(Continued)

*Primary Examiner* — Christopher Koharski
*Assistant Examiner* — James Moss
(74) *Attorney, Agent, or Firm* — Maschoff Brennan (57) ABSTRACT

A system to measure sweat vapor may include a skin contact sensor, a sweat vapor sensor, and a processor. The skin contact sensor may be configured to measure one or more aspects indicative of whether the measuring device is in contact with skin of a user of the measuring device. The sweat vapor sensor may be configured to measure one or more properties of sweat vapor of the user; and the processor may be communicatively coupled to the skin contact sensor and the sweat vapor sensor. The processor may be configured to confirm operation of the measuring device based on the one or more aspects measured by the skin contact sensor, and the sweat vapor sensor receiving the sweat vapor.

15 Claims, 6 Drawing Sheets

(56) References Cited

U.S. PATENT DOCUMENTS

| | | | | |
|---|---|---|---|---|
| 2015/0051473 A1* | 2/2015 | Huang | ................. | A61B 5/0095 |
| | | | | 600/407 |
| 2015/0201853 A1* | 7/2015 | Hong | ................. | A61B 5/02427 |
| | | | | 600/301 |
| 2017/0100035 A1* | 4/2017 | Heikenfeld | ............. | G06F 19/00 |
| 2017/0100072 A1 | 4/2017 | Heikenfeld | | |
| 2017/0102251 A1* | 4/2017 | Masson | ................... | G01D 4/004 |
| 2017/0281877 A1* | 10/2017 | Marlin | .................... | A61M 5/20 |
| 2018/0310988 A1* | 11/2018 | Panescu | ............... | A61B 5/0507 |

OTHER PUBLICATIONS

International Search Report dated Sep. 19, 2018 as received in Application No. PCT/US2018/039510.

Written Opinion of the International Searching Authority dated Sep. 19, 2018 as received in Application No. PCT/US2018/039510.

* cited by examiner

OPERATION-VERIFYING WEARABLE VAPOR SENSOR

FIELD

Some embodiments described herein generally relate to wearable vapor sensors that are capable of confirming their own operation or that increase the accuracy of test results.

BACKGROUND

Unless otherwise indicated herein, the materials described herein are not prior art to the claims in the present application and are not admitted to be prior art by inclusion in this section.

As a person consumes various things, including medications or liquids, such consumption may be observable in the sweat of the person. A vapor sensor can be worn by the person to measure one or more properties of their sweat vapor. Wearable vapor sensors can be used to measure features like compliance with taking of medications. It is desirable to increase the accuracy of readings from such wearable vapor sensors by decreasing the rate of bad sensor readings, for example, from a dirty or blocked sensor. Bad sensor readings may also be the result of tampering with the sensors or intentionally blocking the sensors.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

In an example embodiment, a measuring device may include a skin contact sensor configured to measure one or more aspects indicative of whether the measuring device is in contact with skin of a user of the measuring device. The measuring device may also include a sweat vapor sensor configured to measure one or more properties of sweat vapor of the user, and a processor communicatively coupled to the skin contact sensor and the sweat vapor sensor. The processor may be configured to confirm operation of the measuring device based on the one or more aspects measured by the skin contact sensor, and the sweat vapor sensor receiving the sweat vapor.

In another example embodiment, a method of measuring sweat vapor may include measuring one or more aspects indicative of whether a measuring device is in contact with skin of a user of the measuring device using a skin contact sensor. The method also includes measuring one or more properties of sweat vapor of the user using a sweat vapor sensor. The method also includes confirming operation of the measuring device based on the one or more aspects measured by the skin contact sensor, and the sweat vapor sensor receiving the sweat vapor.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

To further clarify the above and other advantages and features of the present disclosure, a more particular description of the disclosure will be rendered by reference to specific embodiments thereof which are illustrated in the appended drawings. It is appreciated that these drawings depict only typical embodiments of the disclosure and are therefore not to be considered limiting of its scope. The disclosure will be described and explained with additional specificity and detail through the use of the accompanying drawings in which.

DETAILED DESCRIPTION OF SOME EXAMPLE EMBODIMENTS

Some embodiments described herein generally relate to increasing the accuracy of, or confidence in, measurements taken by a measuring device. According to some embodiments, the measuring device may analyze perspiration in the form of sweat vapor of a user to determine one or more properties of the perspiration. As used herein, "sweat vapor" is to be broadly construed to include one or more chemicals and/or chemical compounds emitted at or near a skin surface of a human or non-human (e.g., animal) being and transported there through sweat glands and/or eccrine glands of the skin.

In some embodiments, the measuring device may include a sweat vapor sensor to measure one or more properties of the sweat vapor of the user, and one or more skin contact sensors to measure various aspects that may indicate that the measuring device is in contact with the skin of the user or otherwise verify operation of the measuring device. As used herein, the term "aspect" may include any characteristic or property that may indicate that the measuring device, or any part thereof, is in contact with the skin of a user. Examples of aspects described in the present disclosure may include electrical properties, light properties, air flow properties, water vapor properties, temperature properties, and/or chemical properties. Based on one or more of the aspects measured by the skin contact sensors, the measuring device may make a determination that the measuring device is, or is not, in contact with the skin of the user.

As used herein the term "contact" may include actual physical contact or may include being within a threshold distance from the skin of the user such that the measuring device may receive and measure the one or more properties of the perspiration. The threshold distance from the skin of the user may be based on the particular sensors included in a particular measuring device. The threshold distance from the skin of the user may be a range, for example 0-5.0 millimeters, or 0-3.0 millimeters. The skin contact sensor may be configured to measure the distance from the measuring device to the skin of the user, or an aspect that facilitates determining the distance from the skin. Additionally, the absence of "contact" may include instances in which a sensor is unable to receive sweat vapor from the skin, such as a blocked or clogged sensor.

The measuring device may be included as part of a wearable electronic device that may be embodied as wrist-worn fitness trackers, smartwatches, clip-on ear rings or other ear accessories, hearing aids, dermal patches, armbands, a finger rings, smart watchbands, or other wearable electronic devices. The measuring device may be configured to detect one or more properties of sweat vapor that may correspond to a physical condition of the user, such as blood alcohol content (BAC), smoking or inhaling of second-hand smoke, the use of prescription, controlled, or otherwise restricted substances, blood sugar levels, hydration levels, medical conditions, or other changes in the body chemistry of the user. The wearable electronic device may be similar or comparable or share one or more features with what is disclosed in copending application Ser. No. 15/353,768, filed Nov. 17, 2016, which is herein incorporated by reference in its entirety.

Reference will now be made to the drawings to describe various aspects of some example embodiments of the disclosure. The drawings are diagrammatic and schematic representations of such example embodiments, and are not limiting of the present disclosure, nor are they necessarily drawn to scale.

Figure 1:
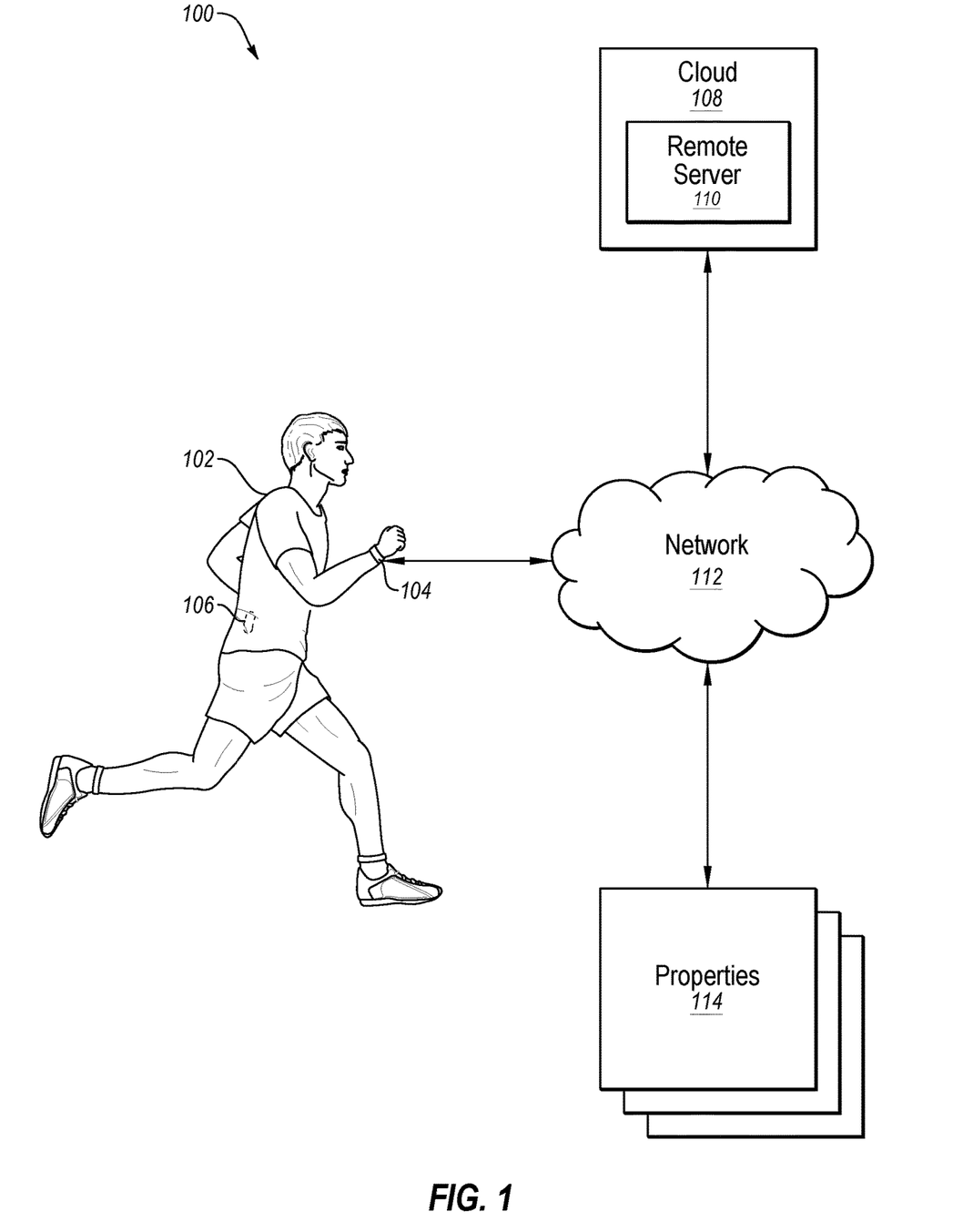
FIG. 1 illustrates an example environment in which some embodiments described herein can be implemented.

FIG. 1 illustrates an example environment 100 in which some embodiments described herein can be implemented. The environment 100 includes a user 102 and a measuring device 104, the measuring device 104 may be included as part of a wearable electronic device. The environment 100 may additionally include a smartphone 106, a cloud computing environment (hereinafter "cloud 108") that includes at least one remote server 110, a network 112, one or multiple properties 114, multiple third parties (not shown) and multiple measuring devices and/or wearable electronic devices (not shown) of the third parties.

The measuring device 104 may be configured to measure one or more properties of sweat vapor of the user 102. Additionally or alternatively, the measuring device 104 may confirm its operation, for example, by verifying that the measuring device 104 is in contact with skin of the user 102. If the measuring device 104 is not operating properly, the measuring device may produce false negative test results, or other inaccurate test results. Some causes of the measuring device 104 not operating properly may include one or more sensors of the measuring device 104 being blocked by sweat crystals, dirt, dead skin cells, tape, or plastic (which may be placed intentionally to block the sensors), or any other matter. Other causes of false negatives include the measuring device being too far from the skin of the user, removed from the user, or transferred to another person or animal. For example, if measuring BAC, the user 102 may place plastic over the measuring device 104 after drinking alcohol to prevent the measuring device 104 from measuring indicators of alcohol in the sweat vapor. In such an example, the measuring device 104 may produce a false negative reading e.g., indicating that no alcohol content or other corresponding property despite the user 102 drinking alcohol. In such a context, it may be advantageous for the measuring device 104 to verify that the measuring device 104 is in contact with the skin of the user 102, or otherwise is working properly.

In some embodiments to verify operation of the measuring device 104, or decrease the rate of false negatives, the measuring device may employ a skin contact sensor (described more fully with reference to FIG. 3) in the process of determining that the measuring device 104 is in contact with the skin of the user 102. If the measuring device 104 determines that the measuring device 104 is not in contact with the skin of the user 102, all measurements and/or test results of the measuring device 104 may be invalidated or called into doubt. Additionally or alternatively, if the measuring device 104 determines that the measuring device 104 is not in contact with the skin of the user 102, the measuring device 104 may notify the user 102, or another party, or suggest that the measuring device 104 may be cleaned or placed closer to skin. The skin contact sensor may include multiple sensors or multiple different types of sensors to increase the likelihood of accurately determining whether the measuring device 104 is in contact with the skin of the user 102.

The network 112 may include one or more wide area networks (WANs) and/or local area networks (LANs) that enable the measuring device 104, the smartphone 106, the cloud 108, the remote server 110, and/or other measuring devices and/or other wearable electronic devices to communicate with each other. In some embodiments, the network 112 includes the Internet, including a global internetwork formed by logical and physical connections between multiple WANs and/or LANs. Alternately or additionally, the network 112 may include one or more cellular RF networks and/or one or more wired and/or wireless networks such as, but not limited to, 802.xx networks, Bluetooth access points, wireless access points, IP-based networks, or the like. The network 112 may also include servers that enable one type of network to interface with another type of network.

According to some embodiments, the measuring device 104 and/or the smartphone 106 may serve as a hub that receives data from the other and/or from discrete sensors and processes the data and/or transmits the data to the cloud 108 for processing. Thus, one or both of the measuring device 104 or the smartphone 106 may include a suitable network connection (e.g., cellular or WAN connection) to send data to and/or receive data from the cloud 108. Alternatively or additionally, the environment 100 may further include a personal computer (PC) dongle, an internet of things (TOT) appliance or other device that receives data from and/or sends data to the measuring device 104 over a relatively limited network connection like Bluetooth and can then transmit data to and/or receive data from the cloud 108 using a cellular connection, WAN connection, or other suitable connection.

The remote server 110 may include a collection of computing resources available in the cloud 108. The remote server 110 may be configured to receive measurements, determinations, calculations, user input, or other information from the measuring device 104, the smartphone 106, a PC dongle, an TOT appliance, or other device in the environment 100.

The environment 100 additionally includes multiple sensors. As described in more detail below, the sensors may include a sweat vapor sensor, and a skin contact sensor.

The measuring device 104 may be embodied in, or part of, one or more wearable electronic devices and may be worn by the user 102. The measuring device may include one or more sensors (e.g., the sweat vapor sensor and/or the skin contact sensor) which may be intended to be in contact with the skin of the user 102 at any of a variety of locations on the body of the user 102. The measuring device 104 may include a user interface to output data to the user 102 and/or to receive input data from the user.

The one or more properties 114 may be one or more aspects that may be measured in the sweat vapor of the user 102. For example, the properties 114 may include concentration of one or more chemicals in sweat vapor, including medication, alcohol, controlled substances, water, and/or others. In some embodiments, the user or a third party may desire to measure a property that may be indirectly measured through the sweat vapor. For example, BAC may not be measured directly in the sweat vapor, but one or more correlated properties may be measured to indirectly measure the desired property. Examples of third parties that may set the properties 114 may include doctors, parole officers, personal trainers, care givers, or others. The properties 114 may be indicators of the existence of a condition.

Figure 2:
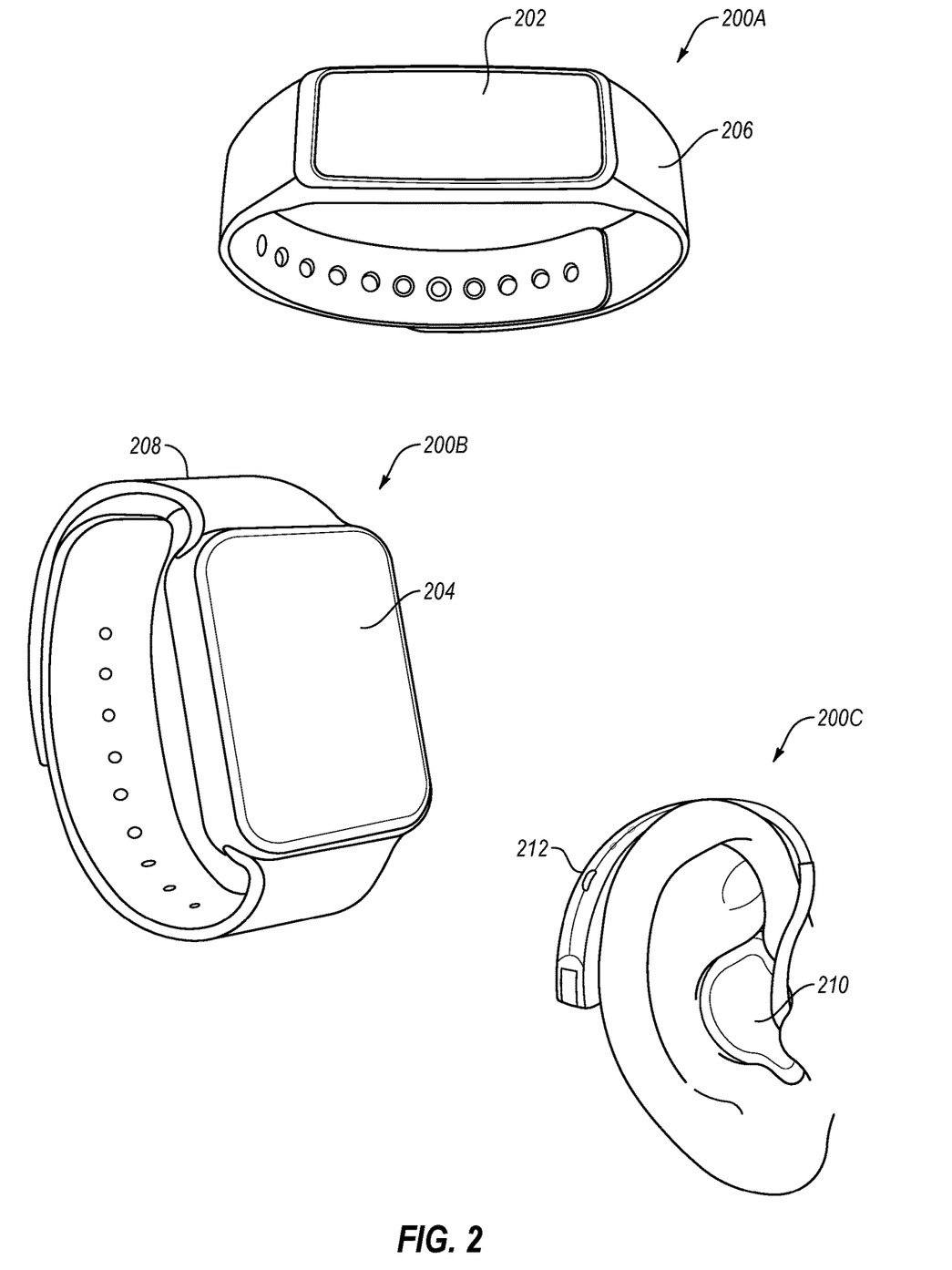
FIG. 2 illustrates various example implementations of a measuring device included in the environment of FIG. 1.

FIG. 2 illustrates various example implementations 200A-200C of the measuring device 104 of FIG. 1, arranged in accordance with at least one embodiment described herein. For instance, and with combined reference to FIGS. 1 and 2, the measuring device 104 of FIG. 1 may be implemented as part of one or more wearable electronic devices, for example a fitness tracker 200A, a smartwatch 200B, or a hearing aid 200C.

The fitness tracker 200A and the smartwatch 200B may typically be worn on a wrist of the user 102 but may alternatively or additionally be worn elsewhere on an arm or leg of the user 102. Each of the fitness tracker 200A and the smartwatch 200B may include an electronics package 202 or 204 with one or more of the sensors described herein integrated therein and located at or near a back side of the electronics package 202 or 204 to be in contact with the skin of the user 102.

Each of the fitness tracker 200A and the smartwatch 200B additionally includes a watchband 206 or 208. Some fitness trackers, smartwatches, and regular watches (e.g., non-smartwatches) have removable watchbands. Embodiments described herein include measuring devices 104 implemented as watchbands in which one or more of the sensors described herein may be integrated therein at or near an inside surface of the watchband. Thus, legacy fitness trackers, smartwatches, and/or regular watches (e.g., devices that lack the sensors described herein to detect sweat vapor and skin contact) can in some embodiments be retrofitted with a watchband that includes one or more of the sensors described herein.

The hearing aid 200C may include at least an inner portion 210 that extends at least partially into an ear canal of the user 102 when in use. The hearing aid 200C may additionally include an outer portion 210 located external to the ear canal of the user 102 when in use. One or more of the sensors described herein may be integrated into the inner portion 210 to be in contact with skin in the ear canal of the user 102. Alternatively or additionally, one or more of the sensors described herein may be integrated into the outer portion 212 to be in contact with skin of the user's outer ear and/or with skin of the user's head.

In some embodiments, a single given user may simultaneously use two or more measuring devices as described herein, each located at different location on the user's body. In some embodiments the measuring device may include multiple sensors in different locations on the body of the user. Information generated by the sensors of the measuring devices may be collected at one of the measuring devices and/or at a smartphone, a PC, the remote server 110 of FIG. 1, and/or other computer device and may be time synchronized to work together.

FIG. 2 illustrates only three example implementations of the measuring device 104 of FIG. 1. In still other embodiments, the measuring device 104 of FIG. 1 may be implemented as a clip-on ear ring or other clip-on ear accessory, a gauged earring, an earring with a pin for pierced ears, eye glasses (e.g., with sensors in nose piece, ear stems, or other location in contact with the skin of the user), a watchband, a dermal patch, an armband, a finger ring, a necklace, footwear (e.g., with sensors in insoles or uppers of shoes, sandals, or other footwear), or other suitable form factor that in at least some embodiments positions corresponding sensors in contact with the skin of the user. Depending on the form factor, detection of sweat vapor and/or properties of the sweat vapor may be detected in sweat vapor excreted as sweat from the skin of the user at the user's ear lobe, ear canal, outer ear, behind the ear, temple, nose, front/back/side of neck or chest, palm of foot, wrist, finger, upper arm, lower arm, upper leg, lower leg, stomach, back, or virtually any other location of the skin of the user.

Figure 3:
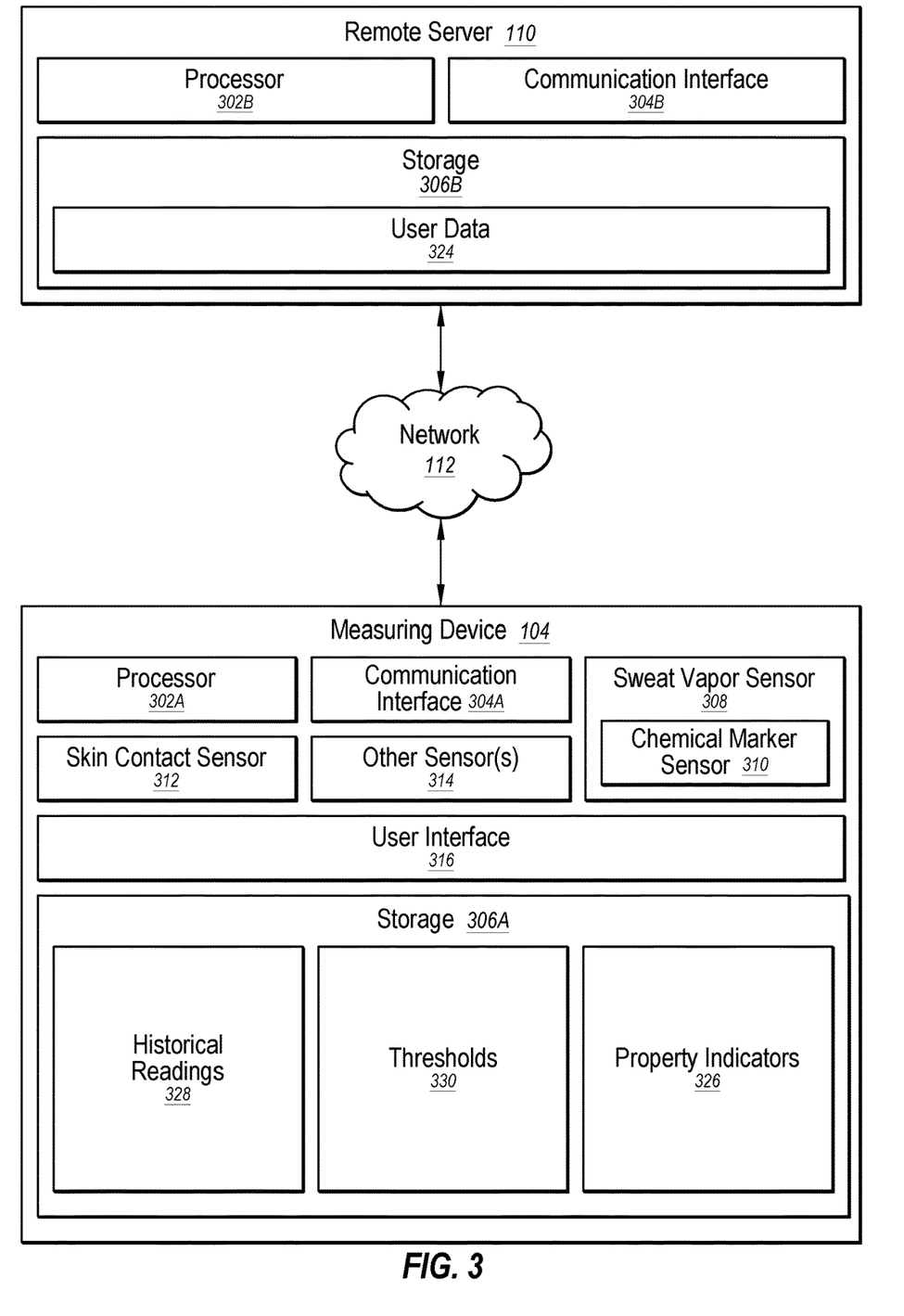
FIG. 3 is a block diagram of the measuring device and a remote server of FIG. 1.

FIG. 3 is a block diagram of the measuring device 104 and remote server 110 of FIG. 1, arranged in accordance with at least one embodiment described herein. Each of the measuring device 104 and the remote server 110 may include a processor 302A or 302B (generically "processor 302" or "processors 302"), a communication interface 304A or 304B (generically "communication interface 304" or "communication interfaces 304"), and a storage and/or memory 306A or 306B (generically "storage 306"). Although not illustrated in FIG. 3, the smartphone 106 of FIG. 1 may be configured in a similar manner as the measuring device 104 as illustrated in FIG. 3. For instance, the smartphone 106 may include the same, similar, and/or analogous elements or components as illustrated in FIG. 3.

Each of the processors 302 may include an arithmetic logic unit, a microprocessor, a general-purpose controller, or some other processor or array of processors, to perform or control performance of operations as described herein. The processors 302 may be configured to process data signals and may include various computing architectures including a complex instruction set computer (CISC) architecture, a reduced instruction set computer (RISC) architecture, or an architecture implementing a combination of instruction sets. Although each of the measuring device 104 and the remote server 110 of FIG. 3 includes a single processor 302, multiple processor devices may be included and other processors and physical configurations may be possible. The processor 302 may be configured to process any suitable number formats including, but not limited to two's compliment numbers, integers, fixed binary point numbers, and/or floating point numbers, all of which may be signed or unsigned.

Each of the communication interfaces 304 may be configured to transmit and receive data to and from other devices and/or servers through a network bus, such as an $I^2C$ serial computer bus, a universal asynchronous receiver/transmitter (UART) based bus, or any other suitable bus. In some implementations, each of the communication interfaces 304 may include a wireless transceiver for exchanging data with other devices or other communication channels using one or more wireless communication methods, including IEEE 802.11, IEEE 802.16, BLUETOOTH®, Wi-Fi, Zigbee, near field communication (NFC), or another suitable wireless communication method.

The storage 306 may include a non-transitory storage medium that stores instructions or data that may be executed or operated on by a corresponding one of the processors 302. The instructions or data may include programming code that may be executed by a corresponding one of the processors 302 to perform or control performance of the operations described herein. The storage 306 may include a non-volatile memory or similar permanent storage media including a flash memory device, an electrically erasable and programmable read only memory (EEPROM), a magnetic memory device, an optical memory device, or some other mass storage for storing information on a more permanent basis. In some embodiments, the storage 306 may also include volatile memory, such as a dynamic random access memory (DRAM) device, a static random access memory (SRAM) device, or the like.

The measuring device 104 may additionally include a sweat vapor sensor 308 and a skin contact sensor 312. In some embodiments, the sweat vapor sensor 308 may include a chemical marker sensor 310. Additionally or alternatively, the measuring device 104 may further include one or more other sensors 314, and a user interface 316.

The sweat vapor sensor 308 may be configured to detect sweat vapor of a user. In some embodiments, the sweat vapor sensor 308 may detect or measure a quantity of sweat vapor at one or more locations. Examples of suitable sweat vapor sensors 308 are marketed by SENSIRION, ST, and BOSCH as humidity and temperature sensors and may include SENSIRION'S SHT31 SENSOR, ST'S HTS221 SENSOR, or BOSCH'S BME280 sensor.

In some embodiments, the sweat vapor sensor 308 may be configured to detect one or more chemical properties of the sweat vapor. For example, the sweat vapor sensor 307 may include the chemical marker sensor 310. In these and other embodiments, the chemical marker sensor 310 may be configured to detect one or more markers in the sweat vapor. The chemical marker sensor 310 may be tuned to a particular marker or may be configured to detect multiple distinct markers. Alternatively or additionally, the chemical marker sensor 310 may be configure detect a quantity, proportion, and/or concentration of one or more markers. In some embodiments, the chemical marker sensor 310 includes a vapor permeable and liquid impermeable membrane to allow sweat vapor to enter into a sensing volume while keeping liquid sweat and/or other potential contaminants out of the sensing volume. The chemical marker sensor 310 may include at least one of a hot plate detector (an example of which is marketed by BOSCH as BOSCH's BME680 sensor), a metal-oxide gas sensor (an example of which is marketed by SENSIRION as SENSIRION's SGPC10 sensor), a graphene nanoelectronic heterodyne sensor, an infrared sensor (e.g., a mid-infrared sensor), or a capacitive micromachined ultrasonic transducer (CMUT)-based chemical sensor. Examples of some of the foregoing are disclosed in the following references which are incorporated herein by reference: (1) Kulkarni, G. S. et al. Graphene nanoelectronic heterodyne sensor for rapid and sensitive vapour detection. Nat. Commun. 5:4376 doi: 10.1038/ncomms5376, (2) U.S. Pat. No. 9,046,650, (3) Lee, H. J., et al. Highly Sensitive Detection of DMMP Using a CMUT-based Chemical Sensor, available at http://stanford.edu/group/khuri-yakub/publications/10_Lee_01.pdf (accessed on Nov. 15, 2016), and (4) Gardner, J. S. et al. CMOS Interfacing for Integrated Gas Sensors: A Review. IEEE Sensors Journal, Vol. 10, No. 12, December 2010.

In some embodiments, the sweat vapor sensor 308 may be configured to measure chemical properties of the sweat vapor and may or may not measure a quantity of sweat, humidity, or temperature. Additionally or alternatively, the sweat vapor sensor 308 may be configured to measure a quantity of sweat, humidity, or temperature and may or may not measure chemical properties of the sweat vapor.

The measuring device 104 may be configured to detect whether the measuring device 104 is properly measuring sweat vapor from the skin of the user. In some embodiments, this may be accomplished by detecting whether the measuring device 104 as a whole, the sweat vapor sensor 308, and/or the skin contact sensor 312 is in contact with the skin using the skin contact sensor 312.

In one or more embodiments, the one or more other sensors 314 may include at least one biometric authentication sensor configured to biometrically authenticate an identity of the user that is using the measuring device 104. The biometric authentication sensor may include at least one of an accelerometer (e.g., for measuring gait), a fingerprint scanner (e.g., for measuring fingerprints), a microphone (e.g., for measuring a voice pattern), an image sensor (e.g., for recognizing a face or an iris), an electrocardiogram (ECG) sensor (e.g., for measuring an ECG), a photoplethysmogram (PPG) sensor (e.g., for measuring a heart rate), or other sensor suitable to generate signals that include or from which can be derived biometric characteristics of the user, referred to as user-specific biometric characteristics. The user-specific biometric characteristics can be compared to biometric characteristics of a particular known person, referred to as person-specific biometric characteristics. The particular known person may be associated with the measuring device 104 and may have the person-specific biometric characteristics generated and stored on in the storage 306A for subsequent biometric authentication. The particular known person may also have, for example, behavioral restrictions or guidelines. Embodiments of the measuring device may detect if users attempt to circumvent accurate measurements of the measuring device by transferring the measuring device to another person. For example, a biometric authentication sensor would detect if the particular known person removed his measuring device and gave it to his designated driver in an attempt to circumvent personal BAC restrictions.

In some embodiments the biometric authentication sensor(s) may work in conjunction with the skin contact sensor 314. For example, the biometric authentication sensor(s) may verify the identity of a user of the measuring device 104 (e.g., by verifying the finger print of the user). After authenticating the user, the measuring device 104 may continuously monitor one or more of the skin contact sensors 314 to verify that the measuring device 104 has been in continuous contact with the skin. In these and other embodiments, the biometric authentication sensor may be used for an initial identity verification and the skin contact sensors 314 may be used for ongoing measurement. Using the ongoing measurement coupled with the identity verification, the measuring device 104 may verify that the various sensors such as the sweat vapor sensor 308 of the measuring device 104 is measuring properties of the sweat vapor of the user whose identity has been verified.

In some embodiments, the measuring device 104 may include a user interface 316. The user interface 316 may be configured to output data to the user and/or to receive input data from the user. The user interface 316 may include at least one of a microphone, a speaker, a display, a touch-screen display, an accelerometer, a button, or other suitable input/output device(s). The measuring device may use the user interface e.g., to suggest that the user: clean the sensors of the measuring device, move to a different location for sensing purposes, undertake an activity, or refrain from an activity. The interface may also be used to receive input in response to suggestions or questions, or to output other data to or receive other data from the user. For example, if sensors on the measuring device detects an abnormally high level of chemical markers related to smoking tobacco, the measuring device may use the interface to suggest that the user clean the sensors of the measuring device, or move to a different location, or cease smoking.

The storage 306A may facilitate the storage of historical readings 328, property indicators 326, and/or thresholds 330.

The historical readings 328 may include measurements from one or more of the sensors 308, 310, 312, 314 and/or information derived therefrom. The historical readings 328 may also include metadata for example, dates, times, locations, and/or time since the most recent measurement.

The property indicators 326 may include indication of the existence (or non-existence) of properties in the sweat vapor, such as the properties 114 of FIG. 1. For example, for the property of the concentration of a chemical X in the sweat vapor, the corresponding property indicator 326 may be "5 ppm." As with the properties 114 of FIG. 1, the property indicators 326 may be based on an indirectly measured property such as BAC. For example, the property indicator 326 may include an indication that the BAC of a user is within a threshold range or below a threshold. The property indicators 326 may relate to determinations as to the existence or degree of one or more conditions. Some examples of chemicals and associated approximate concentrations in sweat vapor may include: sodium (0.9 gram/liter), potassium (0.2 g/l), calcium (0.015 g/l), magnesium (0.0013 g/l), zinc (0.4 milligrams/liter), copper (0.3-0.8 mg/l), iron (1.0 mg/l), chromium (0.1 mg/l), nickel (0.05 mg/l), lead (0.05 mg/l), and/or other trace minerals.

In some embodiments, there may be a logical, temporal or other relationship between the historical readings 328 and the property indicators 326. For example, the historical readings 326 may represent measurements taken at the same time property indicators 326 were determined or when the property indicators 326 indicated a property was present. For example, for a given historical reading associated with the skin contact sensor 312, there may be a corresponding property indicator that indicates whether or not the property was present at the time the historical reading was taken. Additionally or alternatively one or more of the measurements of the historical readings 328 may have contributed to the determination of the property indicators 326.

The thresholds 330 may include any values or ranges for readings from one or more of the sensors 308, 310, 312, 314. For example, the processor 302A of the measuring device 104 may compare readings of one or more of the sensors 308, 310, 312, 314 with a respective threshold. In some embodiments, the thresholds may be associated with the skin contact sensor 312, and may indicate normal operational parameters of the skin contact sensor 312 when the measuring device is in contact with the skin of the user. There may be many thresholds corresponding to many different aspects measured by different skin contact sensors. There may be tiered thresholds representing different levels of normal operational parameters. For example, one temperature threshold may relate to excessive heat, which may indicate that the measuring device is not in contact with the skin of the user. Additionally or alternatively, a second temperature threshold range may relate to normal skin temperatures and may indicate that the measuring device is in contact with the skin of the user. The difference between the threshold and the measurement value may be used to increase or decrease a confidence of a determination that the measuring device 104 is in contact with the skin of the user.

In some embodiments, the thresholds 330 may be pre-configured or preset, for example, by a manufacturer of the measuring device 104. Additionally or alternatively the thresholds 330 may be based on characteristics of the user, or the thresholds 330 may be personalized for the user. For example, the relative dryness of the user's skin may play a role in determining one or more thresholds 330 for that user in determining that the measuring device 104 is operating properly. Additionally or alternatively the thresholds may be adjusted over time for the user.

Referring to the remote server 110, it may include user data 324 and/or other data stored in the storage 306B. The user data 324 may include historical readings 328, property indicators 326, thresholds 330, input date, and/or other data received from measuring devices of multiple users. In some embodiments, the measuring device 104 may provide historical readings 328 to the remote server 110 which may process the historical readings 328 to detect conditions remotely from the measuring device 104. Alternatively or additionally, the remote server 110 may perform more robust or additional or different processing on some or all of the user data 324 than is performed at the measuring device 104. For instance, measuring device 104 may make an initial determination about whether a condition exists based only on historical readings 328 from the skin contact sensor 312 and the sweat vapor sensor 308. In comparison, the remote server 110 may make a final or at least more robust or more involved determination about the condition based on some or all of the foregoing as well as based on subjective input from the user (e.g., subjective input from the user indicating the condition and/or subjective input from the user indicating a self-assessment by the user of the condition), calendar information, objective measurement data indicative of whether an expected effect of the condition is manifest in the user, and/or other information. Alternatively, all of the processing may be performed locally at the measuring device 104.

The skin contact sensor 312 may be any sensor that can measure an aspect that indicates that the measuring device 104 is in contact with the skin of the user. In some embodiments, the skin contact sensor 312 may be implemented as electrodes configured to measure electrical properties between the electrodes, a light sensor, an anemometry device, a sound device, multiple water vapor sensors, a thermometer, chemical sensors or a chemical marker sensor. In some embodiments, the skin contact sensor 312 may include more than one of a given kind of sensor. Additionally or alternatively the skin contact sensor 312 may include multiple different kinds of sensors. For example, the skin contact sensor 312 may include two water vapor sensors and a light sensor. Various examples of the skin contact sensor 312 may be illustrated in FIGS. 4A, 4B, and 5.

Figure 4A:
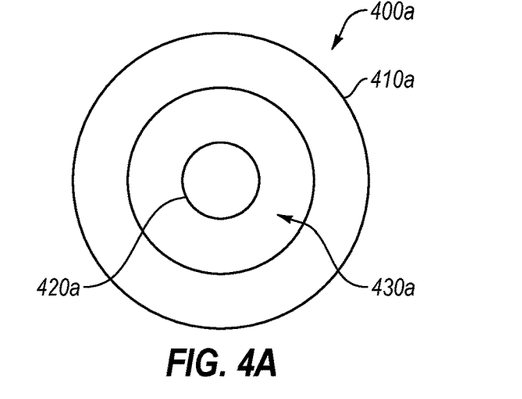
FIGS. 4A-4B illustrate various configurations of sensor elements that form a part of the measuring device of FIG. 1.

FIG. 4A illustrates an example configuration of a skin contact sensor 400a arranged in accordance with at least one embodiment of the present disclosure. The elements of the skin contact sensor 400a may be part of the skin contact sensor 312 of FIG. 3. The elements of the skin contact sensor 400a include an outer electrode 410a, an inner electrode 420a and an insulated or non-contacting region 430a. The inner electrode 410a and the outer electrode 420a may be formed of a material that conducts electricity, such as a metal like copper or gold. The insulated region 430a may be formed of any material that does not conduct electricity, such as an air gap, glass, ceramic, plastic, or rubber.

The skin contact sensor 400a may measure electrical properties that may indicate whether a measuring device, for example measuring device 104 of FIG. 1, is in contact with skin of a user. For example, the skin contact sensor 400a may include two or more electrodes. The electrodes may be configured to measure electrical resistance or conductance between them, for example, by measuring a voltage drop between the two electrodes. The electrical resistance or conductance between the two or more electrodes may indicate that the electrodes are in contact with the skin of the user. For example, if the electrical resistance between the two electrodes is within a range of 10 kilo-Ohms to 10 mega-Ohms, such a resistance may indicate that the electrodes are in contact with the skin of the user. A more limited range may provide a higher confidence reading, for example, if the resistance between the electrodes is within a range of 100 kilo-Ohms to 1 mega-Ohm, such a resistance may indicate with a higher confidence that the electrodes are in contact with the skin of the user. Further, measurements outside a threshold may indicate that the electrodes are not in contact with the skin of the user. For example, resistance between the electrodes that is less than 1 kilo-Ohm or greater than 100 mega-Ohms may indicate that the electrodes are not in contact with the skin of the user.

The elements of the skin contact sensor 400a may be disposed on a wearable electronic device, such as the wearable electronic devices 200A, 200B, and/or 200C of FIG. 2. For example, the elements of the skin contact sensor 400a may be disposed on the back of the fitness tracker 200A, or the smartwatch 200B, or on a portion of the hearing aid 200C that is in contact with the skin of the user.

In some embodiments, a sweat vapor sensor, which may be an implementation of the sweat vapor sensor 308 of FIG. 3 may be disposed between the outer electrode 410a and the inner electrode 420a, or in the center of the inner electrode 420a. In some embodiments, the sweat vapor sensor may form part of the insulated region 430a. Additionally or alternatively, a second skin contact sensor may be disposed between the outer electrode 410a and the inner electrode 420a.

Figure 4B:
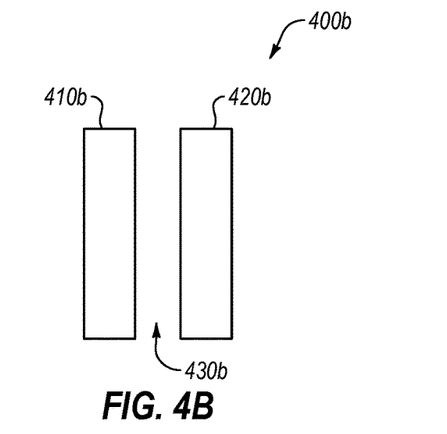

FIG. 4B illustrates another example configuration of a skin contact sensor 400b arranged in accordance with at least one embodiment of the present disclosure. The elements of the skin contact sensor 400b may be part of the skin contact sensor 312 of FIG. 3. The skin contact sensor 400b may be similar or comparable to the skin contact sensor 400a, although with electrodes in an alternative configuration.

The skin contact sensor 400b may include a first electrode 410b (that may be similar or comparable to the first electrode 410a), a second electrode 420b (that maybe similar or comparable to the second electrode 420a), and an insulated region 430b (that may be similar or comparable to the insulated region 430a). The first electrode 410b and the second electrode 420b may be configured to measure electrical properties between the two electrodes, such as a voltage drop or otherwise determine a resistance between the two electrodes.

Figure 5:
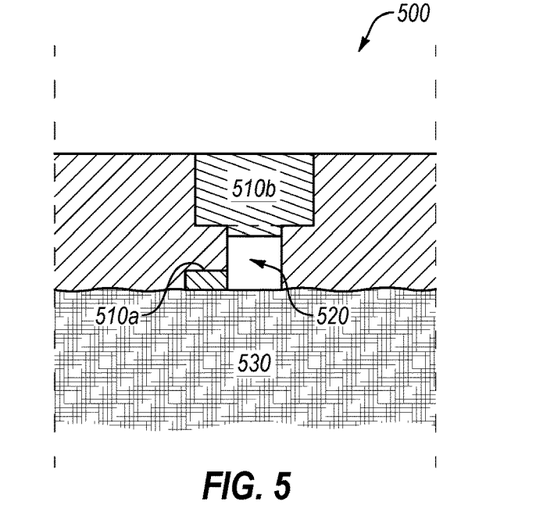
FIG. 5 illustrates a configuration of sensor elements that form a part of the measuring device of FIG. 1.

FIG. 5 illustrates another example configuration of a skin contact sensor 500 arranged in accordance with at least one embodiment described herein. The skin contact sensor 500 may be part of the skin contact sensor 312 of FIG. 3, which may be part of a measuring device such as the measuring device 104 of FIG. 1. The elements of skin contact sensor 500 include a first sensor 510a, a second sensor 510b, and a cavity 520. Skin of a user is illustrated as 530. The first sensor 510a may be in contact with the skin 530. The second sensor 510b may be at least partially disposed within the cavity 520, or a sensitive portion of the sensor 510b may form a part of, or be attached to a wall of the cavity 520. Cavity 520 may be a cavity or recess formed in a surface of the measuring device. Alternatively the cavity 520 may be formed in a protrusion from the surface of the measuring device, similar to a tube protruding from the measuring device.

The skin contact sensor 500 may include a variety of different types of sensors, a few examples of which are described in more detail below. The examples described below include a light sensor, an anemometry device, a sound device, multiple water vapor sensors, a thermometer, chemical sensors, and a chemical marker sensor.

Light Sensor

In some embodiments, the aspect measured by the skin contact sensor 500 may include properties of light that may indicate whether the measuring device is in contact with the skin 530. For example, the skin contact sensor 500 may include a sensor that measures properties of light. The term "light" as used herein may be a general term that refers to visible light, ultraviolet light, infrared (IR) radiation, or other wavelengths of electromagnetic radiation. The light sensor may detect ambient light or the light sensor may be paired with a light source.

The light measured by the light sensor may indicate that the measuring device is in contact with the skin 530. For example, if the light sensor detects too much light, such an aspect may indicate that the measuring device is not in contact with the skin 530. Additionally or alternatively the wavelengths of light detected may indicate whether the measuring is in contact with the skin 530. For example certain wavelengths may be associated with proximity to human skin. For example, human skin may give off, or reflect, certain IR radiation. Additionally or alternatively if the light sensor detects too little light, such an aspect may indicate that the light sensor is blocked, or that part of the measuring device is blocked.

Additionally or alternatively the light sensor may include, or be paired with, a light source, for example a light emitting diode (LED), or an IR LED. In these and other embodiments, the light sensor may detect reflected, or refracted light that was generated by the light source. The light source may be configured to produce light that has specific characteristics that may aid in the determination of whether the measuring device is in contact with the skin of the user. For example, the light sensor may be near the light source and the light sensor may expect certain reflection or refraction characteristics to affect the light after it has been generated by the light source and before it reaches the light sensor. The light sensor may expect certain changes in wavelength, intensity, polarization, or other characteristics. For example, skin may have certain characteristics that affect the properties of the reflected/refracted light that may be distinguishable from how plastic or other blocking material affect the properties of the reflected/refracted light.

In some embodiments, the light sensor may measure changes in the reflections over time. For example the light sensor may detect heartbeats of the user based on recurring changes in the reflections. Additionally or alternatively, the light sensor may use a delay between time the light source generates the light and the time the reflected or refracted light arrives at the light sensor to determine whether the measuring device is in contact with the skin 530.

In some embodiments, the light sensor may be in contact with the skin 530, as illustrated by the first sensor 510*a*, in which case the second sensor 510*b* may or may not be omitted. Additionally or alternatively, the light sensor may be within a cavity 520 as illustrated by the second sensor 510*b*, in which case the first sensor 510*a* may or may not be omitted. Additionally or alternatively the light source may be positioned in contact with the skin 530 or within the cavity 520. One advantage of positioning the light sensor within the cavity 520, as illustrated by the second sensor 510*b*, is that the light sensor may be configured to detect if there were a blockage or occlusion of the cavity 520. Such a configuration may be particularly useful if a sensor of another type is used along with the light sensor at the back of the cavity 520 in the position of the second sensor 510*b*.

Anemometry Device

In some embodiments, the aspect measured by the skin contact sensor 500 may include air flow properties that may indicate whether the measuring device is in contact with the skin 530. For example, the skin contact sensor 500 may include an anemometry device. The anemometry device may be configured to measure air flow. The air flow at the anemometry device may indicate that the measuring device is in contact with skin 530. For example, if the anemometry device measures no air flow, such an aspect may indicate that at least a part of the measuring device has been blocked. Additionally or alternatively if the anemometry device measures an air flow that is too large, such an aspect may indicate that the anemometry device is not in contact with the skin 530. In some embodiments, the anemometry device may be positioned within the cavity 520 where the sweat vapor is expected to flow, as illustrated by the second sensor 510*b*. The cavity 520 may extend through the whole measuring device to enable air flow from proximate the skin 530 out and away from the user.

In some embodiments, the anemometry device may include a laser that measures the flow of air via a spectroscopic approach or speckle analysis, for example Laser Doppler Anemometry (LDA). Additionally or alternatively, the anemometry device may include a mechanical device, system, component, or combinations thereof for measuring air flow, for example a pinwheel or weather vane. The mechanical device, system, component, or combinations thereof for measuring air flow may be small or even microscopic in scale, for example, a micro-machined weather vane. The air measured may include sweat vapor. In some embodiments, the anemometry device may include or be paired with a source of air flow that pushes or puffs air to a location.

Sound Device

In some embodiments, the aspect measured by the skin contact sensor 500 may include sound measurements that may indicate whether the measuring device is in contact with the skin 530. For example, the skin contact sensor 500 may include a sound device which may measure sound. The sound device may include a speaker, a microphone, or a transducer configured to both generate and measure sound. The term "sound" as used herein may be a general term which describes vibrations of air molecules or changes of air pressure at frequencies within, above or below the range of human hearing. The term "sound" may also include vibrations of the skin of the user. The sound device may make measurements that may indicate whether the measuring device is in contact with skin 530. For example, the sound device may generate a sound pulse directed toward the skin 530 and measure the sound reflected back to the sound device. The time of delay between generating the sound pulse and receiving the reflection may be used to determine whether the measuring device is in contact with skin 530. Additionally or alternatively, the sound device may measure changes in the sound pulse reflected back to the sound device. Additionally or alternatively, the sound device may measure sounds related to the user, for example a heartbeat.

In these and other embodiments, the sound device may positioned within the cavity 520 as illustrated by the second sensor 510*b*. Such a configuration may be advantageous for time delay calculations. In some embodiments the sound device may be positioned in contact with the skin 530 as illustrated by the first sensor 510*a*. Such a configuration may be advantageous for detecting differences between the generated sound and the reflected sound that is transmitted and reflected in the user's skin 530, or detecting the heart beat or other sounds from the skin 530.

Water Vapor Sensors

In some embodiments, the aspect measured by the skin contact sensor 500 may be related to water vapor properties that may indicate whether the measuring device is in contact with the skin 530. For example, the skin contact sensor 500 may include two or more water vapor sensors and/or temperature sensors to measure a water vapor gradient. The water vapor sensors may be configured to measure a difference in water vapor between the two sensors (e.g., between one pair of sensors) such that a determination regarding a water vapor gradient may be made. In these and other embodiments, one or more of the water vapor sensors may be implemented as the sweat vapor sensor 308 of FIG. 3.

One water vapor sensor may be in contact with the skin 530 as illustrated by the first sensor 510*a*, and a second water vapor sensor may be within the cavity 520 as illustrated by the second sensor 510*b*. The pair of water vapor sensors may then measure a water vapor gradient that may indicate that the skin contact sensor 500 is in contact with skin 530 and/or that the sweat vapor is passing into the cavity 520.

Thermometer

In some embodiments, the aspect measured by the skin contact sensor 500 may include temperature properties that may indicate whether the measuring device is in contact with the skin 530. For example, the skin contact sensor 500 may include a thermometer. The thermometer may be any device, system, component, or combinations thereof for measuring temperature, including a mercury thermometer, a thermistor, a silicon bandgap thermometer, or an IR thermometer. The temperature measurements of the thermometer may indicate that the measuring device is in contact with skin 530. For example temperature measurements within a threshold, such as 97 to 100 degrees Fahrenheit may indicate that the measuring device is in contact with the skin 530.

In some embodiments, the thermometer may be positioned in contact with the skin 530 as illustrated by the first sensor 510*a*. Additionally or alternatively, the thermometer (or a second thermometer) may be positioned within the cavity 520 as illustrated by the second sensor 510*b*.

Chemical Marker Sensor

In some embodiments, the aspect measured by the skin contact sensor 500 may include chemical marker properties that may indicate whether the measuring device is in contact with the skin 530. For example, the skin contact sensor 500 may include a chemical marker sensor such as the chemical marker sensor 310. The chemical marker sensor may include any device, system, component, or combinations thereof for measuring the presence of chemical markers, including those described above with relation to chemical marker sensor 310. The chemical marker measurements of the chemical marker sensors may indicate that the measuring device is in contact with the skin 530. For example, the chemical marker sensor may detect the presence of chemical markers in concentrations that indicate that the chemical marker sensor is measuring sweat and therefore the chemical marker sensor is in contact with the skin 530. As another example, the chemical marker sensor may detect the presence of chemical markers of proteins or other chemicals associated with skin (e.g., collagen).

The chemical marker sensor may be positioned close to the skin 530 as illustrated by the first sensor 510*a*. Additionally or alternatively, the chemical marker sensor (or a second chemical marker sensor) may be positioned within the cavity 520 as illustrated by the second sensor 510*b*.

Returning to FIG. 5 generally, in some embodiments, the measuring device may include multiple skin contact sensors 500. In these or other embodiments, the skin contact sensor 500 may include multiple sensors, including multiple types of sensors, to measure different aspects at one or more different locations. For example, the skin contact sensor 500 may include a pair of electrodes outside of the cavity 520 and an IR detector within the cavity 520. Each additional sensor added to a measuring device may increase the accuracy of the determination that the measuring device is in contact with the skin 530.

As one example of using multiple sensors, a user may accidentally inhibit the operation of his measuring device by getting it dirty, with sweat, grease, dust or the like. Multiple skin contact sensors 500 may increase the ability of the measuring device to determine whether the measuring device is in contact with the skin 530. For example, a pair of electrodes may indicate that the measuring device is in contact with skin but an anemometer device may indicate that the measuring device is not in contact with skin. Conflicting results from the multiple sensors may indicate that the measuring device is not operating normally. In some embodiments, the conflicting results may invalidate, or decrease the confidence of any measurements or determinations of the other sensors of the measuring device. In these and other embodiments, based on the measuring device not operating properly, the user may be prompted to clean his device, check the device, or take the device to a third party (e.g., a technician, a physician, a parole officer, etc.).

As another example of using multiple sensors, a user may intentionally try to inhibit the operation of a measuring device with multiple sensors. The user may try to induce false negative readings, e.g., to indicate that the user is not intoxicated when the user has been drinking by blocking sensors of the measuring devices with tape, a sleeve, or by attaching his measuring device to simulated skin. For example, it may be possible that the user may be able to mimic skin contact for one or more skin contact sensors 500 by attaching the measuring device to a warm water bladder at a comparable temperature to a human being such that a reading of a thermometer (one of the skin contact sensors) may indicate that the measuring device is in contact with the skin 530 when it is not in contact with the skin 530. However, an increasing number of skin contact sensors 500, or an increasing number of different types of sensors in the skin contact sensors 500, may increase the difficulty of manipulating the measuring device. For example, a pair of electrodes may measure that the resistance between the two electrodes is higher than the resistance for skin and may thus indicate that the measuring device is not in contact with the skin 530.

For some circumstances or use cases, a single sensor or a single type of sensor in the skin contact sensor 500 may be sufficient. For example, a parent may want a simple device with a single skin contact sensor to deter their child from trying to tamper with readings in a simple measuring device. For other circumstances or use cases, multiple sensors, or multiple types of sensors for the skin contact sensor 500 may be utilized. For example, a professional sports organization may want a more complex device to prevent or deter tampering with readings in measuring devices for their players.

Figure 6:
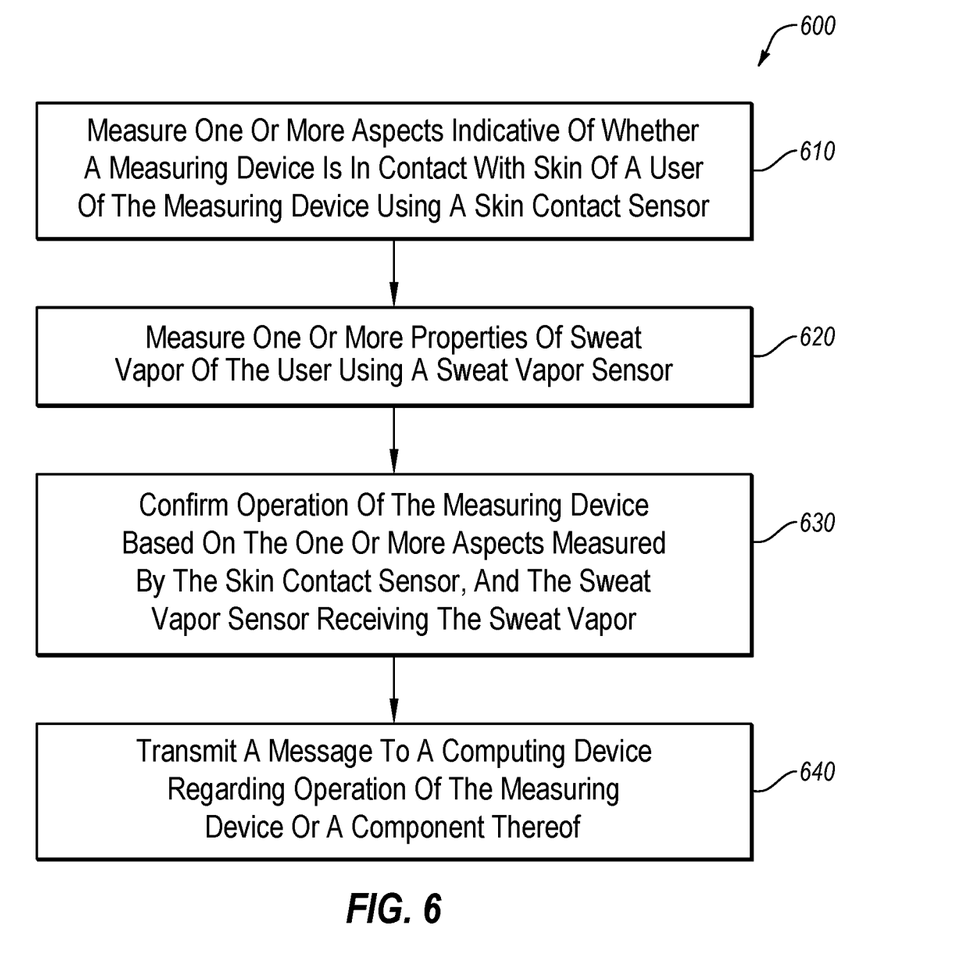
FIG. 6 includes a flow chart of an example method to confirm operation of the measuring device.

FIG. 6 is a flowchart of an example method 600 to measure sweat vapor, arranged in accordance with at least one embodiment described herein. The method 600 may be implemented, in whole or in part, by the measuring device 104, the smartphone 106, and/or the remote server 110 described elsewhere herein. Alternatively or additionally, software in the form of computer-executable instructions stored in one or both of the storage 306A or 306B of FIG. 3 may be executed by one or both of the processor 302A or 302B to cause the corresponding processor 302A and/or 302B to perform or control performance of one or more of the operations or blocks of the method 600. The method 600 may include one or more of blocks 610, 620, 630, and/or 640. The method 600 may begin at block 610.

At block 610, measurements may be taken of one or more aspects that may be indicative of whether the measuring device is in contact with skin of a user. For example, readings of a skin contact sensor (such as the skin contact sensor 312 of FIG. 3) may indicate whether the measuring device is in contact with the skin of the user. Block 610 may include measuring one or more aspects via one or more of the skin contact sensors described above. The block 610 may be followed by block 620.

At block 620, sweat vapor of the user may be measured using a sweat vapor sensor of the measuring device. Measuring the sweat vapor of the user may include detecting a quantity, volume, chemical components, or other measurement of the sweat vapor of the user using a sweat vapor sensor (such as the sweat vapor sensor 308 of FIG. 3). Alternatively or additionally, detecting the sweat vapor of the user may include detecting the sweat vapor from at least one of: a wrist of the user, an ear canal of the user, or an ear lobe of the user. In other embodiments, sweat vapor may not be detected such that block 620 may be omitted, for example, if the sweat vapor sensor is blocked or is too far from the skin of the user. In these and other embodiments, an attempt may be made, even if unsuccessful, to measure sweat vapor. Stated another way, a reading may be taken from the sweat vapor sensor even though the sweat vapor sensor may not actually be sensing sweat vapor. Block 620, or block 610 if block 620 is omitted, may be followed by block 630.

At block 630, a determination may be made concerning whether the measuring device is operating as expected. The determination may be based on the aspects measured by the skin contact sensors of block 610 and/or the receipt of sweat vapor in block 620. In some embodiments, the determination may be based on aspects being within thresholds. The determinations may be a confidence level, or a score, rather than an exclusively binary determination. Block 630 may be followed by block 640.

At block 640, a message may be transmitted to a computing device regarding operation of the measuring device or a component thereof. For example, the measuring device may transmit an indication of its operation, or the operation of any or each of its individual sensors or components to the computing device. Such a block may include sending a message to a remote device or routing the message to a display to be displayed to the user.

In some embodiments, such a message may request the user to perform an action associated with the measuring device. Such an action may facilitate the presence or absence of a given measurement. For example, the user may receive a message instructing the user to remove the measuring device and then put back on the measuring device. Such an action may have an expected response (e.g., a baseline sensor reading of no contact followed by contact), and if that expected response does not occur, it may be determined that a sensor is malfunctioning.

Figure 7:
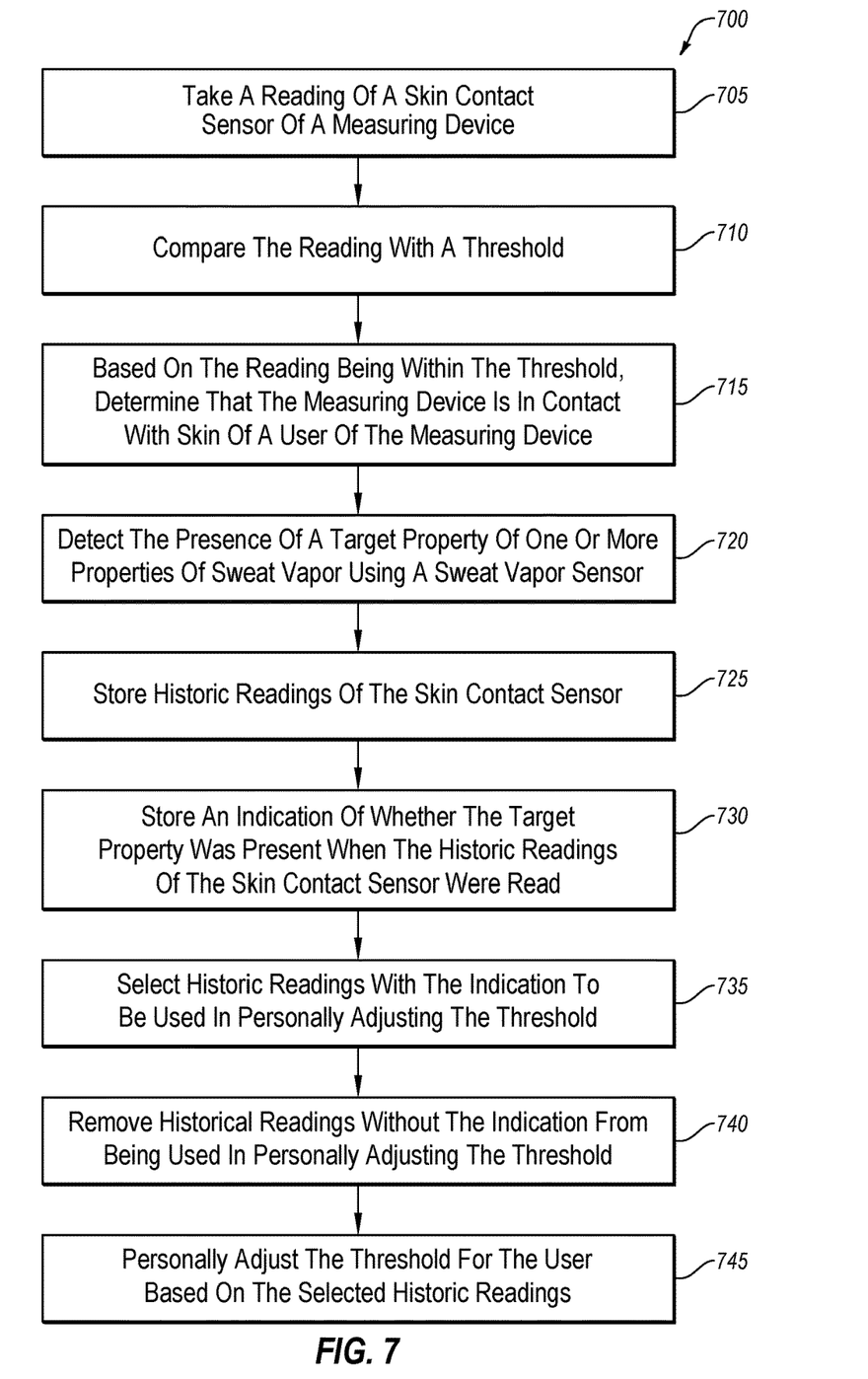
FIG. 7 includes a flow chart of an example method to adjust thresholds to confirm operation of the measuring device, all arranged in accordance with at least one embodiment described herein.

FIG. 7 is a flowchart of an example method 700 to measure sweat vapor, arranged in accordance with at least one embodiment described herein. The method 700 may be implemented, in whole or in part, by the measuring device 104, the smartphone 106, and/or the remote server 110 described elsewhere herein. Alternatively or additionally, software in the form of computer-executable instructions stored in one or both of the storage 306A or 306B of FIG. 3 may be executed by one or both of the processor 302A or 302B to cause the corresponding processor 302A and/or 302B to perform or control performance of one or more of the operations or blocks of the method 700. The method 700 may include one or more of blocks 705, 710, 715, 720, 725, 730, 735, 740, and/or 745. The method 700 may begin at block 705.

At block 705, measurements may be taken of one or more aspects that may be indicative of whether the measuring device is in contact with skin of the user. For example, detecting aspects indicating whether the measuring device is in contact with the skin of the user may include taking readings or measurements from a skin contact sensor (such as the skin contact sensor 312 of FIG. 3). Block 705 may include taking one or more readings from one or more of the skin contact sensors described above. The block 705 may be followed by block 710.

At block 710, the measurements may be compared with one or more thresholds (such as the thresholds 330 of FIG. 3 related to the skin contact sensor or sensors). Block 710 may include making one or more comparisons based on measurements from one or more skin contact sensors. The block 710 may be followed by block 715.

At block 715, a determination may be made concerning whether the measuring device is in contact with the skin of the user based on the comparison between the one or more measurements and the thresholds. The determination may be based on aspect measurements being within thresholds. Aspect measurements being within thresholds may indicate either that the measuring device is in contact with the skin of the user, or that the measuring device is not in contact with the skin of the user, depending on the threshold. The determinations may be a confidence level or a score rather than exclusively binary. The block 715 may be followed by block 720.

At block 720, the presence of one or more properties are detected by a sweat vapor sensor, including a target property. The properties of sweat vapor may include indications of conditions for which the measuring device is configured to measure, such as blood alcohol content (BAC), smoking or inhaling of second-hand smoke, the use of prescription, controlled, or otherwise restricted substances, lactate levels, the presence of (or levels of) cortisol, blood sugar levels, hydration levels, medical conditions, or other changes in the body chemistry of the user. Other properties of the user may also be measured such as an elevated heart rate, or body temperature. The properties of sweat vapor may be similar or comparable to the properties 114 of FIG. 1. The presence the target property may be a binary determination, or it may be represented by a score, confidence level, a concentration or a representation of to what extent the property is present. For example the presence of the target property may be a determination that the user is intoxicated, additionally or alternatively the property may be a measurement that the user's BAC is 0.08. The block 720 may be followed by block 725.

At block 725, historic readings of the skin contact sensor may be stored. For example historical readings 328 of FIG. 3 may be stored. The historical readings may be stored in any storage, such as one or more of the storages 306 of FIG. 3. The block 725 may be followed by block 730.

At block 730, an indication of whether the target property was present when the historic readings of the skin contact sensor were read may be stored. The indication of the presence of the target property may be similar or analogous to the property indicators 326 of FIG. 3. In some embodiments, the properties and the aspects may be measured by the sweat vapor sensors and the skin contact sensors respectively at about the same time. Additionally or alternatively, a property may be measured at one time and be known to persist while an aspect is measured. At block 730 an indication of whether the target property was present may be stored with historic readings from the skin contact sensors. For example, the property of BAC of 0.0 may be the target property and one or more historical readings taken while the BAC is 0.0 for the user may be stored with an indication that the BAC was within the threshold when the historical readings were taken. The block 730 may be followed by block 735. Additionally or alternatively, a confidence score associated with the reading may be stored with the historic readings. For example, one or more readings may yield a confidence score for whether or not the measuring device is in contact with the skin of the user and/or if the measuring device is operating properly. For example, for a measuring device with multiple sensors like a resistance measuring device and a humidity measuring device, the reading for each sensor may indicate a confidence score for whether or not the measuring device is operating properly and/or is contact with the skin. As another example, a coordinated set of values may be associated with the multiple sensors such that someone attempting to cheat the measuring device would have the entire coordinated set of values to attempt to fake.

At block 735, historic readings that are coincident with an indication that the target property was present may be selected for the purpose of personally adjusting the thresholds. For example, the historical readings taken when the BAC of the user was 0.0 may be selected. The block 735 may be followed by the block 740.

At block 740, historic readings that are not coincident with an indication that the target property was present may be excluded from use in personally adjusting the thresholds. For example, historical readings taken when the BAC of the user was higher than 0.0 (e.g., 0.2 or above) may be excluded. The block 740 may be followed by the block 745. Thus, block 735 and/or block 740 may be used to select for consideration, or remove from consideration, historical readings based on the presence or absence of the target property.

At block 745, the thresholds for the user may be adjusted based on the historic readings. The thresholds may be analogous to the thresholds 330 of FIG. 3. The historic readings that are used in adjusting the thresholds may be exclusively the historic readings that coincide with the presence of the target property because of the operation of block 735 and/or block 740. Alternatively, all historic readings may be used to adjust the thresholds without regard for the target property. Thresholds may be set and adjusted based on baseline readings of the skin contact sensors.

Adjusting the thresholds for the user may improve the accuracy of the determination that the skin contact sensor is in contact with the skin of that user by tuning the skin contact sensor for that user. For example, if the user has dry skin, or lives in a dry climate, the skin contact sensor may measure aspects that are consistently influenced by the dry skin or the dry climate. As such, the aspects measured by the skin contact sensor may be outside a typical range or biased towards a portion of the typical range. If the aspects measurements of that user are consistently measured to be within a particular range, it may be advantageous to adjust the threshold for that user to improve consistency and/or accuracy of determining that the measuring device is in contact with the skin of the user. As another example, a user who is properly hydrated will have lower skin resistance compared to a person who is not properly hydrated. For a user who consistently fails to properly hydrate, the threshold resistance for that user may be personalized to be higher as compared to a person who properly hydrates.

Furthermore, adjusting the thresholds based on the presence or absence of a target property may further increase the accuracy and consistency of the confirmation that the measuring device is functioning properly. For example, an elevated heart rate may be coincident with increased perspiration. For example, a first threshold may be set based on a target property of a low heart rate, and the first threshold may not be adjusted based on readings taken when the user has an elevated heart rate. Alternatively, it may be advantageous to have separate thresholds based on different target properties, e.g., the first threshold for a low heart rate and a second threshold for a high heart rate.

In some embodiments, by excluding historical readings that are not coincident with an indication that the target property was present, the accuracy may be further improved. Using the example of BAC, a user is unlikely to attempt to tamper with their device when their BAC is 0.0. Thus, by only using historical readings where the BAC is 0.0 may facilitate personalization with readings that have not been tampered with.

In these and other embodiments, historical readings from certain time periods may also be selectively utilized. For example, if a user is a social drinker and works an office job from the hours of nine in the morning to five in the evening, it is less likely that the user is drinking alcohol from ten until eleven in the morning, and readings from that time period may be used in determining a baseline or threshold value.

A single user may have multiple different personalized thresholds for multiple different aspects measured by skin contact sensors.

In some embodiments, the biometric authentication may work cooperatively with the skin contacting sensor of the measuring device. For example, the biometric authentication device may verify the identity of the user of the measuring device. After verifying the identity of the user, the measuring device may continue to monitor that the measuring device is in contact with the skin of the user of the measuring device. In these and other embodiments, the readings of the skin contact sensor may utilize a personalized threshold to continue to detect whether the measuring device is in contact with the skin.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Some embodiments described herein have generally been described as processing information generated by sensors and/or information derived therefrom at a measuring device to determine proper operation of the measuring device. Alternatively or additionally, the information generated by the sensors and/or information derived therefrom may be processed exclusively at a smartphone such as the smartphone 106 of FIG. 1, at a remote server such as the remote server 110 of FIG. 1, or at another computer device to determine proper operation of the measuring device. Alternatively or additionally, the information generated by the sensors and/or information derived therefrom may be processed at two or more of a measuring device, a smartphone, a remote server, or other computer device to determine the existence of a condition.

Embodiments disclosed herein have generally been described in the context of determining whether the measuring device is in contact with the skin of the user. The determination of the measuring device is in contact with the skin of the user may be a proxy for determining that the measuring device is functioning properly and has not been tampered, or blocked. Alternatively or additionally, embodiments described herein may be implemented in making a measuring device tamper-resistant or deterring users from tampering with their measuring devices.

The present disclosure is not to be limited in terms of the particular embodiments described herein, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that the present disclosure is not limited to particular methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." The terms "about" or "approximately" may include within 10% of a value, for example, "about 5" may include 4.5 to 5.5.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A measuring device, the device comprising:
a skin contact sensor configured to measure one or more aspects indicative of whether the measuring device is in contact with skin of a user of the measuring device;
a sweat vapor sensor configured to measure one or more properties of sweat vapor of the user, the sweat vapor sensor distinct from the skin contact sensor;
a storage device, communicatively coupled to the skin contact sensor and the sweat vapor sensor, the storage device configured to store historic readings of the skin contact sensor and historic properties of the sweat vapor corresponding to the historic readings of the skin contact sensor taken at a same time; and
a processor communicatively coupled to the skin contact sensor, the sweat vapor sensor, and the storage device, the processor configured to perform operations comprising:
selecting a subset of the historic readings of the skin contact sensor, the subset selected based on the historic properties corresponding to the subset of the historic readings indicating that a target property of the one or more properties of the sweat vapor was present when the historic readings were taken, the target property corresponding to a condition related to body chemistry of the user;
adjust a threshold to be specific to the user based on the subset of the historic readings of the skin contact sensor; and
confirm operation of the measuring device based on:
the one or more aspects indicative of whether the measuring device is in contact with the skin of the user as measured by the skin contact sensor satisfying the adjusted threshold indicating that the measuring device is in contact with the skin of the user as measured after adjusting the threshold to the adjusted threshold; and
the sweat vapor sensor receiving the sweat vapor.

2. The measuring device of claim 1, wherein the skin contact sensor includes a pair of electrodes and is configured to measure resistance between the pair of electrodes.

3. The measuring device of claim 1, wherein the skin contact sensor includes an infrared (IR) sensor and is configured to measure IR radiation from the user.

4. The measuring device of claim 1, further comprising a cavity configured for the sweat vapor to flow therethrough, wherein the skin contact sensor includes an anemometry device disposed in the cavity and configured to detect movement of the sweat vapor passing through the cavity.

5. The measuring device of claim 4, wherein the anemometry device includes a laser.

6. The measuring device of claim 1, further comprising a cavity, wherein the skin contact sensor includes a first water vapor sensor in a first portion of the cavity and a second water vapor sensor in a second portion of the cavity, wherein the processor is configured to measure a concentration gradient between the first water vapor sensor and the second water vapor sensor.

7. The measuring device of claim 1, wherein the skin contact sensor includes a thermometer and is configured to measure temperature.

8. The measuring device of claim 1, wherein the sweat vapor sensor includes a chemical marker sensor and wherein a profile of chemical markers is compared to readings from the chemical marker sensor.

9. The measuring device of claim 1, further comprising a second skin contact sensor, each of the skin contact sensor and the second skin contact sensor includes one or more of a pair of electrodes, an IR sensor, an anemometry device, at least two water vapor sensors, a thermometer, a chemical sensor and a chemical marker sensor.

10. The measuring device of claim 9, wherein a reading of the skin contact sensor is utilized to adjust a threshold associated with the second skin contact sensor.

11. The measuring device of claim 1, further comprising a communication device to transmit a message to a computing device indicating one or more of whether the one or more properties of the sweat vapor were detected in the sweat vapor, whether the measuring device is in contact with the skin, and whether the measuring device has confirmed operation.

12. The measuring device of claim 1, further comprising a biometric authentication sensor configured to verify an identity of the user of the measuring device in an initial identity verification and the skin contact sensor is used in an ongoing measurement to verify that the measuring device is in continuous contact with the skin of the user such that the sweat vapor sensor is measuring one or more properties of the sweat vapor of the user of the initial identity verification because the measuring device has been in continuous contact with the skin of the user.

13. A method of measuring sweat vapor, the method comprising:
measuring one or more aspects indicative of whether a measuring device is in contact with skin of a user of the measuring device using a skin contact sensor;
storing readings of the skin contact sensor;
measuring one or more properties of sweat vapor of the user using a sweat vapor sensor distinct from the skin contact sensor;
storing properties of sweat vapor corresponding to the readings of the skin contact sensor taken at a same time;
selecting a subset of the stored readings of the skin contact sensor, the subset selected based on the stored properties corresponding to the subset of the stored readings indicating that a target property of the one or more properties of the sweat vapor was present when the stored readings were taken, the target property corresponding to a condition related to body chemistry of the user;
adjusting a threshold to be specific to the user based on the subset of the stored readings of the skin contact sensor; and
confirming operation of the measuring device at a later time after the threshold has been adjusted, based on:
the one or more aspects indicative of whether the measuring device is in contact with the skin of the user as measured by the skin contact sensor satisfying the adjusted threshold indicating that the measuring device is in contact with the skin of the user as measured after adjusting the threshold to the adjusted threshold; and
the sweat vapor sensor receiving the sweat vapor.

14. The method of claim 13, further comprising:
removing a second set of readings of the skin contact sensor from the subset based on the stored readings of the sweat vapor sensor corresponding to the second set of readings of the skin contact sensor indicating absence of the target property corresponding to the condition related to the body chemistry of the user.

15. The method of claim 13, further comprising communicating whether the one or more properties of sweat vapor were detected in the sweat vapor to a computing device.

* * * * *